US008338379B2

(12) United States Patent
Yamaguchi et al.

(10) Patent No.: US 8,338,379 B2
(45) Date of Patent: Dec. 25, 2012

(54) MONOCLONAL ANTIBODY AND USE THEREOF

(75) Inventors: Haruyasu Yamaguchi, Maebashi (JP); Noriaki Kinoshita, Takasaki (JP); Masahiro Maeda, Takasaki (JP); Yuko Horikoshi, Takasaki (JP)

(73) Assignee: Intellect Neurosciences, Inc., New York, NY (US)

( * ) Notice: Subject to any disclaimer, the term of this patent is extended or adjusted under 35 U.S.C. 154(b) by 0 days.

(21) Appl. No.: 12/888,661

(22) Filed: Sep. 23, 2010

(65) Prior Publication Data

US 2011/0008339 A1 Jan. 13, 2011

Related U.S. Application Data (63) Continuation of application No. 10/589,969, filed as application No. PCT/JP2004/013536 on Sep. 16, 2004, now Pat. No. 7,807,157.

(30) Foreign Application Priority Data

Feb. 20, 2004 (JP) ................................ 2004-045111

(51) Int. Cl.
*C07K 16/00* (2006.01)
*A01N 37/18* (2006.01)
(52) U.S. Cl. ................... 514/17.8; 514/17.7; 530/388.1; 530/388.25; 530/387.3
(58) Field of Classification Search ........................ None
See application file for complete search history.

(56) References Cited

U.S. PATENT DOCUMENTS

| 5,437,995 A | 8/1995 | Ichimori et al. |
| 2003/0073655 A1 | 4/2003 | Chain |
| 2005/0152903 A1 | 7/2005 | Newman et al. |

FOREIGN PATENT DOCUMENTS

| EP | 0125023 | 11/1984 |
| EP | 0239400 | 9/1987 |
| EP | 0683234 | 11/1995 |
| WO | 9007861 | 7/1990 |
| WO | 9417197 | 8/1994 |
| WO | 9420632 | 9/1994 |
| WO | 0072876 | 12/2000 |

OTHER PUBLICATIONS

Matthews et al., "Calpain Activity Regulates the Cell Surface Distribution of Amyloid Precursor Protein", The Journal of Biological Chemistry, vol. 277, No. 39, pp. 36415-36424 (2002).

Vandermeeren et al., "The Functional Y-Secretase Inhibitor Prevents Production of Amyloid β 1-34 in Human Murine Cell Lines", Neuroscience Letters, vol. 315, No. 3, pp. 145-148 (2001).
Matthews et al., "Alzheimer's Disease-Related Overexpression of the Cation-Dependent Mannose 6-Phosphate Receptor Increases Aβ Secretion". The Journal of Biological Chemistry, vol. 277, No. 7, pp. 5299-5307 (2002).
Janus, Christopher et al. "Aβ Peptide Immunization Reduces Behavioural Impairment and Plaques in a Model of Alzheimer's Disease", Letters to Nature, vol. 408, No. 6815, pp. 978-983 (2000).
Tamaoka, Akira, "Alzhemer-Byo no Kotal Ryoho", Gendal Iryo, vol. 34, No. 1, pp. 237-244 (2002).
Kinebuchi et al., "A novel Cell Surface Antigen Involved in Thymocyte and Thymic Epithelial Cell Adhesion", The Journal of Immunology, vol. 146, No. 11, pp. 3721-3728 (1991).
Frenkel et al., "High Affinity Binding of Monoclonal Antibodies to the Sequential Epitope EFRH of Beta-amyloid Peptide is Essential for Fibrillar Aggregation." Journal of Neuroimmunology, 95:136-142 (1999).
Horikoshi et al., "Development of A-beta Terminal End-specific Antibodies and Sensitive ELISA for A-beta Variant." Biochemical and Biophysical Research Communications 319:733-737 (2004).
Yamaguchi et al., "Diffuse Plaques Associated With Astroglial Amyloid Beta Protein, Possibly Showing a Disappearing Stage of Senile Plaques." Acta Neuropathol 95:217-222 (1998).
Morishima-Kawashima et al., "Effect of Apolipoprotein E Allele ε4 on the Initial Phase of Amyloid β-Protein Accumulation in the Human Brain", American Journal of Pathology, vol. 157, No. 6, pp. 2093-2099 (2000).
Erlanger et al., "Steroid-Protein Conjugates", Departments of Microbiology, Biochemistry, and Obstetrics and Gynecology, Collage of Physicans, Columbia University, vol. 234, No. 5, pp. 1090-1094 (1958).
Karu et al., "Synthesis of Haptens and Derivation of Monoclonal Antibodies for Immunoassay of the Phenylurea Herbicide Dluron", J. Agric. Food Chem., vol. 42, No. 2, pp. 301-309 (1994).
Yazaki et al., "Humanization of the Anti-CEA T84.66 Antibody Based on Crystal Structure Data", Protein Engineering, Design & Selection, vol. 17, No. 5, pp. 481-489 (2004).
Carter et al., "Humanization of an Anti-p185HER2 Antibody for Human Cancer Therapy", Proc. Natl. Acad. Sci., vol. 89, pp. 4285-4289 (1992).
Tobinasi et al., "Feasibility and Pharmacokinetic Study of a Chimeric Anti-CD-20 Monoclonal Antibody (IDEC-C2B8, Rituximab) in Relapsed B-Cell Lymphoma. The IDEC-C2B8 Study Group", Ann. Oncol., vol. 9, No. 5, pp. 1-2 (1998).

*Primary Examiner* — Olga N Chernyshev
(74) *Attorney, Agent, or Firm* — Fish & Richardson P.C.

(57) ABSTRACT

An antibody capable of recognizing amyloid β while not recognizing amyloid β precursor proteins, and a method for using the same.
A monoclonal antibody characterized by being capable of recognizing the N-terminus peptide of amyloid β while not recognizing amyloid β precursor proteins, an amyloid β assay kit, a therapeutic agent of Alzheimer's disease, and a method for treating Alzheimer's disease using the monoclonal antibody.

10 Claims, 9 Drawing Sheets

MONOCLONAL ANTIBODY AND USE THEREOF

CROSS REFERENCE TO PRIOR APPLICATIONS

This application is a continuation application of U.S. Ser. No. 10/589,969, filed Aug. 18, 2006, which is the U.S. National Phase under 35 U.S.C. §371 of International Patent Application No. PCT/JP2004/013536, filed Sep. 16, 2004, and claims the priority of Japanese Patent Application No. 2004-045111, filed Feb. 20, 2004. Each of the aforementioned applications is hereby incorporated herein by reference in its entirety. The International Application published in Japanese on Sep. 1, 2005 as WO 2005/080435 under PCT Article 21(2).

REFERENCE TO SEQUENCE LISTING

Pursuant to 37 C.F.R. 1.821(c), a sequence listing is submitted herewith as an ASCII compliant text file named "Sequence Listing.txt" that was created on Sep. 23, 2010, and has a size of 1,798 bytes. The content of the aforementioned file named "Sequence Listing.txt" is hereby incorporated by reference in its entirety.

TECHNICAL FIELD

The present invention relates to a monoclonal antibody which can recognize the N-terminus peptide of an amyloid β, but not an amyloid β precursor protein, and a method of using the monoclonal antibody.

BACKGROUND ART

An amyloid β is a peptide consisting of 40 or 42 amino acids and is generated from an amyloid β precursor protein (APP) cleaved by β-selectase and γ-selectase. The amyloid β with 40 amino acids is referred to as amyloid β (1-40) and the amyloid β with 42 amino acids is referred to as amyloid β (1-42). The amino acid sequences of the amyloid β (1-40) and amyloid β (1-42) are as follows.

```
Amyloid β (1-40) (Amino acid sequence No. 5)
DAEFRHDSGYEVHHQKLVFFAEDVGSNKGAIIGLMVGGVV Amyloid β (1-42) (Amino acid sequence No. 6)
DAEFRHDSGYEVHHQKLVFFAEDVGSNKGAIIGLMVGGVVIA
```

Of these amyloids β, the amyloid β (1-40) is reported to be a peptide cleaved via a common metabolic pathway and to have weak toxicity. On the other hand, the amyloid β (1-42) is said to be insoluble, have strong toxicity, easily agglomerate into a fibrous form, and be accumulated in the brain and cause Alzheimer's disease.

Therefore, assaying each amyloid β peptide is very important in diagnosing Alzheimer's disease and investigating the mechanism of Alzheimer's disease occurrence.

Heretofore, an amyloid β antibody has been used for assaying an amyloid β (for example, Patent Document 1). However, since the amyloid β antibody described in the Patent Document 1 has an epitope in the 3-8 site of the amino acid sequence of the amyloid β, an amyloid β assay kit using this antibody detects amyloid β precursor proteins (APP), as well as amyloid β (1-40) and amyloid β (1-42) possessing the entire length of amino acid sequence. A presently commercially available amyloid β antibody ("6E10" manufactured by Signet Laboratories, Inc.) also recognizes APP.

In addition, a method of suppressing accumulation of amyloid β in the brain in order to prevent Alzheimer's disease has been investigated. However, since the presently known amyloid β antibodies react not only with an amyloid β, but also APP in normal cells, these antibodies have high possibility of causing side reaction such as inflammation and, therefore, have not been clinically applied.

Patent Document 1: WO 1994/017197 pamphlet

DISCLOSURE OF THE INVENTION

Problems to be Solved by the Invention

Accordingly, a first object of the present invention is to provide an antibody capable of recognizing an amyloid β, but not APP.

A second object of the present invention is to provide a system for precisely assaying amyloid β (1-40) and amyloid β (1-42) which completely possess the entire length, by using the antibody.

A third object of the present invention is to provide a therapeutic agent and the like for Alzheimer's disease comprising the above antibody as an active ingredient.

Means for Solving the Problems

As a result of extensive studies in order to solve the above first object, the inventors of the present invention have found that an antibody which can recognize an amyloid β, but not APP, can be obtained by immunizing with a specific peptide.

In addition, as a result of extensive studies in order to solve the above second object, the inventors have found that a system that can precisely assay amyloid (1-40) and amyloid β (1-42) which completely possess the entire length (the amyloid (1-40) and amyloid β (1-42) are hereinafter referred to from time to time collectively as "amyloids β") can be constructed by using the above antibody.

In addition, as a result of extensive studies in order to solve the above third object, the inventors have found that the above antibody can inhibit deposition of amyloids β and can be used for treatment of Alzheimer's disease.

Specifically, a first invention is to provide a monoclonal antibody which can recognize the N-terminus peptide of amyloid β, but not amyloid β precursor proteins.

A second invention is to provide a kit for assaying amyloids β comprising a first reagent containing an antibody which can recognize the N-terminus peptide of amyloids β, but not amyloid β precursor proteins and a second reagent containing an antibody which can recognize amyloid β (1-40) or amyloid β (1-42).

A third invention is to provide a method for assaying amyloids β comprising causing an antibody which can recognize the N-terminus peptide of an amyloid β, but not amyloid β precursor proteins, and an antibody which can recognize amyloid β (1-40) or amyloid β (1-42) to react with an amyloid β in a sample to be assayed.

A fourth invention is to provide a method for producing the above monoclonal antibody comprising immunizing an animal with a bound substance of the N-terminus peptide of an amyloid β and a biological high molecular compound as a first antigen and immunizing the thus-immunized animal with a bound substance of another N-terminus peptide of an amyloid β, which is comparatively shorter than the peptide used for the first antigen, and a biological high molecular compound as a second antigen, and collecting the antibody from the animal.

A fifth invention is to provide a therapeutic agent for Alzheimer's disease comprising the above monoclonal antibody as an active ingredient.

A sixth invention is to provide a deposition inhibitor of amyloid β (1-40) or amyloid β (1-42) comprising the above monoclonal antibody as an active ingredient.

A seventh invention is to provide a method of treatment of Alzheimer's disease comprising administering the above monoclonal antibody.

An eighth invention is to provide a method of inhibiting deposition of amyloid β (1-40) or amyloid β (1-42) comprising administering the above monoclonal antibody.

Effect of the Invention

The monoclonal antibody of the present invention recognizes the N-terminus peptide of an amyloid β, but not an amyloid β precursor protein.

Therefore, the use of this antibody makes it possible to construct a system for precisely assaying amyloid β (1-40) and amyloid β (1-42) which completely possess the entire length, which has been impossible heretofore.

In addition, since the antibody can suppress deposition of amyloids β in the brain, it is possible to safely treat Alzheimer's disease.

BEST MODE FOR CARRYING OUT THE INVENTION

It is difficult to obtain the monoclonal antibody of the present invention which can recognize the N-terminus peptide of amyloid β, but not amyloid β precursor proteins (hereinafter referred to as "N-terminus antibody") by immunizing an animal with an N-terminus peptide of an amyloid β using a conventional technique. Because the amino acid sequence of the amyloid β is completely identical with a part of the amyloid β precursor proteins, it is difficult to obtain an antibody that can distinguish the amyloid β from the precursor proteins.

Therefore, in order to obtain the N-terminus antibody of the present invention, it is necessary to immunize an animal with a bound substance of the N-terminus peptide of an amyloid β and a biological high molecular compound as a first antigen and immunize the thus-immunized animal with a bound substance of another N-terminus peptide of an amyloid β, which is comparatively shorter than the peptide used for the first antigen, and a biological high molecular compound as a second antigen, and collect the antibody from the animal.

The method for preparing the N-terminus antibody of the present invention using the above-mentioned first antigen and second antigen will be described below.

The N-terminus peptide of the amyloid β used for the first antigen is a peptide consisting of a continuous amino acid sequence from the N-terminus to the C-terminus of the amino acid sequence of amyloid β (1-40) or amyloid β (1-42) (Sequence ID No. 5 or Sequence ID No. 6), preferably a peptide consisting of amino acid sequence 1 to 28 of the amyloid β, and particularly preferably a peptide containing amino acid sequence 1 to 16 of the amyloid β which is shown by the following amino acid sequence (a).

(a) DAEFRHDSGYEVHHQK (SEQ ID No. 1)

The peptide consisting of the above amino acid sequence can be obtained by various methods without any specific limitations. Such a peptide may be synthesized by a method known in the art or a synthetic peptide commercially available from Synpep Corporation, TANA Laboratories, USA, etc. may be used.

The peptide consisting of the above amino acid sequence is bound with a biological high molecular compound and the resulting bound substance is used as a first antigen. The peptide is preferably bound after attaching cysteine (C) to the amino acid at the C-terminus.

As examples of the biological high molecular compound bound with the peptide, keyhole limpet hemocyanin (KLH), ovalbumin (OVA), bovine serum albumin (BSA), rabbit serum albumin (RSA), thyroglobulin, and the like can be given. Of these, KLH and thyroglobulin are preferable.

The above-mentioned peptide can be bound with the biological high molecular compound by a known method such as a mixed acid anhydride method (B. F. Erlanger, et al., J. Biol. Chem., 234, 1090-1094 (1959)), an activated ester method (A. E. KARU, et al., J. Agric. Food Chem., 42, 301-309 (1994)), and the like.

A mixed acid anhydride used in the mixed acid anhydride method is obtained by subjecting the above-mentioned peptide to a common Schotten-Baumann reaction. The resulting reaction product is reacted with the biological high molecular compound to obtain the target bound substance of the peptide and biological high molecular compound. As examples of the haloformate used in this mixed acid anhydride method, methyl chloroformate, methyl bromoformate, ethyl chloroformate, ethyl bromoformate, and isobutyl chloroformate can be given. The ratio of the peptide, haloformate, and high molecular compound used in this method can be appropriately selected from a wide range.

The Schotten-Baumann reaction is carried out in the presence of a basic compound. As the basic compound used for the reaction, compounds commonly used in the Schotten-Baumann reaction, for example, organic bases such as triethylamine, trimethylamine, pyridine, dimethylaniline, N-methylmorpholine, diazabicyclononene (DBN), diazabicycloundecene (DBU), and diazabicyclooctane (DABCO), inorganic bases such as potassium carbonate, sodium carbonate, potassium hydrogencarbonate, and sodium hydrogencarbonate; and the like can be used.

The reaction is carried out at a temperature usually from −20° C. to 100° C., and preferably from 0° C. to 50° C., for 5 minutes to 10 hours, and preferably 5 minutes to 2 hours.

The reaction of the resulting mixed acid anhydride and the biological high molecular compound is carried out at a temperature usually from −20° C. to 150° C., and preferably from 0° C. to 100° C., for 5 minutes to 10 hours, and preferably 5 minutes to 5 hours. The mixed acid anhydride method is usually carried out in a solvent. Any solvents commonly used in the mixed acid anhydride method, for example, halogenated hydrocarbons such as dichloromethane, chloroform, and dichloroethane; aromatic hydrocarbons such as benzene, toluene, and xylene; ethers such as diethyl ether, dioxane, tetrahydrofuran, and dimethoxyethane; esters such as methyl acetate and ethyl acetate; aprotic polar solvents such as N,N-dimethylformamide, dimethyl sulfoxide, and triamide hexamethylphosphate, and the like can be given.

On the other hand, the activated ester method can be carried out as follows. First, the peptide is dissolved in an organic solvent and reacted with imide N-hydroxysuccinate in the presence of a coupling agent to produce activated imide N-hydroxysuccinate.

As the coupling agent used in this reaction, any coupling agents commonly used in a condensation reaction, for example, dicyclohexylcarbodiimide, carbonyldiimidazole, water-soluble carbodiimide, and the like can be used. As an organic solvent, for example, N,N-dimethylformamide (DMF), dimethyl sulfoxide, dioxane, and the like can be used. The molar ratio of the peptide and the coupling agent such as imide N-hydroxysuccinate used for the reaction is preferably from 1:10 to 10:1, and most preferably 1:1. The reaction is carried out at a temperature usually from 0° C. to 50° C., and preferably from 22° C. to 27° C., for 5 minutes to 24 hours, and preferably 1 to 2 hours. A reaction temperature not lower than the melting point, but not higher than the boiling point of the reactants is preferable.

After the coupling reaction, the reaction solution is added to and reacted with a solution in which the biological high molecular compound is dissolved to produce, for example, when the biological high molecular compound has a free amino group, an acid amide bond between the amino group and the carboxyl group in the above peptide. The reaction is carried out at a temperature usually from 0° C. to 60° C., preferably from 5° C. to 40° C., and more preferably from 22° C. to 27° C., for 5 minutes to 24 hours, preferably 1 to 16 hours, and more preferably 1 to 2 hours.

The reaction products obtained by any of the above methods are purified by dialysis, desalting column, and the like to obtain a bound substance of the peptide and biological high molecular compound (hereinafter referred to from time to time as "bound substance 1").

The N-terminus peptide of the amyloid β comparatively shorter than the peptide used for the first antigen, which is used for the second antigen is a peptide consisting of a continuous amino acid sequence from the N-terminus to the C-terminus of the amino acid sequence of amyloid β similar to the peptide used for the first antigen. There are no specific limitations to such a peptide insofar as the length is shorter than the length of the peptide used for the first antigen, with a peptide of which the length is shorter by 3 to 11 amino acids, preferably 5 to 11 amino acids, than the peptide used for the first antigen being preferable. As such a peptide, a peptide consisting of amino acid sequence 1-13 of amyloid β is preferable, with a more preferable peptide being that consisting of amino acid sequence 1-11 of amyloid β. A peptide shown by the following amino acid sequence (b) which contains amino acid sequence 1-5 of the amyloid β is particularly preferable.

(b)　　　DAEFR　　　(Sequence ID No. 2)

The above peptide can produce a bound substance with a biological high molecular compound (hereinafter referred to from time to time as "bound substance 2") in the same manner as the method for producing the bound substance 1.

Next, the method for preparing the N-terminus antibody using the bound substance 1 and the bound substance 2 obtained in this manner as antigens will be described. Any known method for preparing the antibody, such as a method described in, for example, Immunobiochemical Research Method in the Sequel Biochemical Experiment Lecture (edited by the Japanese Biochemical Society) can be appropriately used, except for the use of the bound substance 1 and the bound substance 2.

In order to prepare the N-terminus antibody of the present invention using the above bound substances, an animal is first immunized using the bound substance 1 as a first antigen, the immunized animal is immunized using the bound substance 2 as a second antigen, and the resulting antibody is collected from the animal.

As a specific immunization method, the following can be given. First, the bound substance 1 is dissolved in a sodium phosphate buffer solution (PBS). Next, the solution is mixed with a Freund's complete adjuvant, incomplete adjuvant, or an assisting agent such as alum to obtain a first antigen, with which an animal is immunized.

As the animal to be immunized, any animals commonly used in the art, for example, mammals such as a mouse, rat, rabbit, goat, and horse can be used. The method of administering the immunogen for the immunization may be subcutaneous injection, intraperitoneal injection, intravenous injection, intradermal injection, or intramuscular injection, with subcutaneous injection and intraperitoneal injection being preferable. For immunization, the immunogen is administered one time or two or more times at an appropriate interval, preferably two or more times at an interval of one to five weeks.

Subsequently, the animal immunized with the first antigen in this manner is immunized with a second antigen, which is prepared using the bound substance 2 in the same manner as in the first antigen. In the same manner as in immunizing with the first antigen, the immunogen is administered one time or two or more times at an appropriate interval, preferably two or more times at an interval of one to five weeks.

Finally, immunocytes obtained from the immunized animal is fused with myeloma cells according to a conventional method to obtain a hybridoma. The monoclonal antibody to the N-terminus of amyloid β can be obtained by collecting the antibody from the hybridoma culture.

The N-terminus antibody of the present invention obtained in this manner can be used as an immunoassay reagent or a therapeutic agent for Alzheimer's disease.

For use as a reagent for immunoassay, it is desirable to label or immobilize the antibody, if necessary.

In order to label the antibody, a labeling substance such as enzymes (horseradish peroxidase (HRP), alkaline phosphataze, etc.), fluorescent substances (fluoresceine isocyanate, rhodamine, etc.), radioactive materials (32P, 125I, etc.), chemoluminescence substances, and the like is bound with the N-terminus antibody. In order to immobilize the N-terminus antibody, the antibody is bound with an appropriate immobilizing medium. Any immobilizing media conventionally used in the immunochemical measuring method, for example, a plate such as a 96-well microtiter plate made from polystyrene, an amino group-bonded microtiter plate, etc., and various types of beads can be used. In order to immobilize the N-terminus antibody, a buffer solution containing the antibody, for example, is added to a carrier and incubated.

The N-terminus antibody of the present invention can be used as a reagent for precisely assaying amyloid β by combining particularly with an antibody recognizing amyloid β (1-40) or amyloid β (1-42).

As the antibody recognizing amyloid β (1-40) or amyloid β (1-42) to be combined with the N-terminus antibody of the present invention, a polyclonal antibody or a monoclonal antibody that can be obtained using a part or whole of the amino acid sequence of the amyloid β (1-40) or amyloid β (1-42) as an antigen by a conventional method, for example, can be used. Of these antibodies, an antibody recognizing the C-terminus peptide of the amyloid β (hereinafter referred to as "C-terminus antibody") is preferable due to the accuracy of the assay.

The C-terminus antibody is not specifically limited so long as the antibody can recognize the C-terminus peptide of the amyloid β (1-40) or amyloid (1-42) to be assayed. It is, however, desirable that the antibody does not recognize an amyloid β other than the amyloid β (1-40) or amyloid β (1-42) to be assayed, such as an amyloid β (1-43), for example.

Specifically, the C-terminus antibody recognizing the amyloid β (1-40) (hereinafter referred to as "C-terminus antibody 1") can be obtained by a conventional method using a peptide (C-terminus peptide) consisting of a continuous amino acid sequence from the C-terminus to the N-terminus of the amyloid β (1-40) (Sequence ID No. 5) as an antigen. More specifically, C-terminus peptide used as an antigen is preferably a peptide consisting of amino acid sequence 18-40 of amyloid β (1-40), and particularly preferably amino acid sequence 35-40 of amyloid β (1-40) shown by the following amino acid sequence (c).

(c)    MVGGVV    (Sequence ID No. 3)

In the same way, the C-terminus antibody recognizing the amyloid (1-42) (hereinafter referred to as "C-terminus antibody 2") can be obtained by a conventional method using a peptide consisting of a continuous amino acid sequence from the C-terminus to the N-terminus of the amyloid β (1-42) (Sequence ID No. 6) as an antigen. More specifically, the peptide used as an antigen is preferably a peptide consisting of amino acid sequence 18-42 of amyloid β (1-42), and particularly preferably amino acid sequence 38-42 of amyloid β (1-42) shown by the following amino acid sequence (d).

(d)    GVVIA    (Sequence ID No. 4)

In addition, when preparing the C-terminus antibody using the above peptide, a bound substance of the peptide with a biological high molecular compound may be used as an antigen in the same way as in the preparation of the N-terminus antibody. In this bound substance of the peptide with a biological high molecular compound, the peptide is preferably bound after attaching lysine-cysteine (KC), for example, to the amino acid at the N-terminus.

As the antibody recognizing amyloid β (1-40) or amyloid β (1-42), the following antibodies commercially available from Immuno-Biological Laboratories Co., Ltd. can be used.

Anti-Human Amyloid β (35-40) (1A10) Mouse IgG MoAb (Product number: 10047)

Anti-Human Amyloid β (1-40) Rabbit IgG Affinity Purify (Product number: 18580)

Anti-Human Amyloid β (1-42) Rabbit IgG Affinity Purify (Product number: 18582)

Amyloid β (1-40) or amyloid β (1-42) can be precisely assayed by using the N-terminus antibody of the present invention and the antibody recognizing the amyloid β (1-40) or amyloid β (1-42). As specific assay methods, various methods currently used in common immunochemical measuring such as radioisotope immunoassay (RIA method), ELISA method (E. Engvall et al. (1980), Methods in Enzymol., 70, 419-439), fluorescent antibody technique, plaque method, spot method, condensation method, Ouchterlony, immunochromatography, and the like ("Hybridoma method and monoclonal antibody" R&D Planning Inc., pp 30-53, Mar. 5, 1982) can be used.

Although an appropriate method can be selected from these assay methods taking various factors into consideration, the ELISA method is preferable due to the high sensitivity, ease of assaying, and the like. A specific procedure of assaying amyloid β will be described taking a sandwich method, which is one of the ELISA methods, as an example.

As a step (A), an antibody recognizing amyloid β (1-40) or amyloid β (1-42) is immobilized on a carrier. Next, as a step (B), the surface of the carrier on which the antibody is not immobilized is blocked with a substance irrelevant to amyloid β, for example, a protein. As a step (C), test samples containing amyloid β at different concentrations are added to produce a complex of amyloid β and the antibody. Then, as a step (D), the labeled N-terminus antibody of the present invention is added to combine the N-terminus antibody with the complex of amyloid β and the antibody. Finally, as a step (E), the amount of the substance used as a label is measured to determine the amount of amyloid β in the sample using a previously prepared calibration curve. Although the measurement is possible when the antibody used in the step (A) and the antibody used in the step (D) are reversed, immobilization of the antibody recognizing amyloid β (1-40) or amyloid β (1-42) is more preferable from the viewpoint of detection sensitivity.

There are no specific limitations to the carrier used for immobilizing the antibody recognizing amyloid β (1-40) or amyloid β (1-42) in the step (A). Any carriers commonly used in immunochemical assay can be used. For example, a 96-well microtiter plate made of polystyrene or an amino group bound-type microtiter plate can be given. In order to immobilize the above antibody, a buffer solution containing the antibody, for example, is added to a carrier and incubated. As the buffer solution, known buffer solutions such as a 10 mM PBS can be given. Although the concentration of the antibody in the buffer solution can be selected from a wide range, usually a range from about 0.01 to 100 µg/ml, and preferably from 0.1 to 20 µg/ml is used. When a 96-well microtiter plate is used as a carrier, the volume per well is 300 µl or less, and preferably about 20 to 150 µl. There are also no specific limitations to the incubation conditions. Usually, incubation overnight at about 4° C. is appropriate.

Blocking in step (B) is to inhibit amyloid β in a test sample from being adsorbed in the carrier, on which the antibody has been immobilized in the step (A), irrespective of the antigen-antibody reaction. As a blocking agent, BSA, a skim milk solution, and commercially-available blocking agents such as "Block Ace" manufactured by Dainippon Pharmaceutical Co., Ltd. (code No. UK-25B) can be used, for example. Although not limited, a specific blocking method comprises, for example, adding an appropriate amount of Block Ace to a portion in which an antigen has been immobilized and incubating overnight at about 4° C., followed by washing with a buffer solution.

Further, the test sample containing an amyloid β is caused to come in contact with an immobolized antibody and the amyloid β is captured with the immobilized antibody to produce a complex of the immobilized antibody and the amyloid β in the step (C). The conditions for producing the complex is not limited. The reaction is conducted at about 4 to 37° C. for about 1 hour to overnight. After the reaction, the carrier is preferably washed with a buffer solution to remove unreacted proteins and the like. As the buffer solution, a 10 mM PBS (pH 7.2) containing 0.05% (v/v) Tween 20 is preferable.

Further, in step (D), a labeled antibody which recognizes an epitope of the amyloid β captured by the immobilized antibody other than the epitope bonded to the immobilized antibody is added to produce a complex of the immobilized antibody, amyloid β, and the labeled antibody. After the reaction, the carrier is preferably washed with a buffer solution to remove unreacted proteins and the like. The same buffer solution as that described above is used for this reaction. The amount of the labeled antibody used in step (D) is about 5,000 to 10,000 times that of the immobilized antibody, preferably an amount diluted to a concentration in which the ultimate absorbance is 1.5-2.0. A buffer solution can be used for dilution and the reaction is carried out at about 4 to 37° C. for about 1 hour, for example. After the reaction, the complex substance is preferably washed with the buffer solution. The complex of the immobilized antibody, amyloid β, and the labeled antibody is formed by the above reaction.

In step (E), a coloring substrate solution reactive with the labeling substance in the complex of the immobilized antibody, amyloid β, and the labeled antibody is added and absorbance is measured to calculate the amount of amyloid β in reference to a calibration curve.

When peroxidase, which is an enzyme, is used for labeling the antibody, a coloring substrate solution containing hydrogen peroxide and 3,3',5,5'-tetramethylbenzine (hereinafter referred to as "TMB") can be used, for example. Although not limited, the coloring reaction is carried out by adding the coloring substrate solution, reacting at about 25° C. for about 30 minutes, and adding a 1-2 N sulfuric acid aqueous solution to terminate the enzyme reaction. When TMB is used, the coloration is determined by measuring absorbance at 450 nm. When alkaline phosphatase enzyme is used as a labeling substance, on the other hand, p-nitrophenylphosphoric acid is used as a coloring substrate, a 2N NaOH solution is added to terminate the enzyme reaction, and the absorbance at 415 nm is measured. The concentration of amyloid β in a sample can be calculated by using a calibration curve previously prepared using the absorbance of a reaction solution to which amyloid 13 with a known concentration is added.

In order to assay amyloid β according to the method described above, a kit for assaying amyloids β comprising a first reagent containing the N-terminus antibody of the present invention and a second reagent containing an antibody which can recognize amyloid β (1-40) or amyloid β (1-42) is preferably used. Such a kit is hereinafter referred to as "kit of the present invention".

The kit of the present invention can be prepared according to a conventional method. Specifically, the N-terminus antibody of the present invention or an antibody which recognizes amyloid β (1-40) or amyloid β (1-42) as a labeled antibody, and a buffer solution for dilution, a standard substance, a buffer solution for a substrate, a termination solution, washing fluid, and the like are combined.

An amyloid β (1-40) or amyloid β (1-42) completely possessing the entire length in samples such as plasma and serum can be precisely assayed using the assay kit obtained in this manner and the above measuring method.

In addition, since the N-terminus antibody of the present invention can recognize the N-terminus peptide of an amyloid β, but not an amyloid β precursor protein, the N-terminus antibody can selectively bond to the amyloid β and inhibit deposition thereof. Therefore, the N-terminus antibody of the present invention can be used for treatment of diseases induced by accumulation of amyloid β, preferably as a therapeutic agent for Alzheimer's disease which is induced by accumulation of amyloid β in the brain.

In order to use the N-terminus antibody of the present invention as a therapeutic agent for Alzheimer's disease, the N-terminus antibody is purified, if necessary, and made into a preparation by a conventional method. There are no specific limitations to the form of the therapeutic agent for Alzheimer's disease. For example, the agent may be a fluid preparation (injection preparation). For forming the preparations, carriers and additives conforming to the form of the preparation can be used to the pharmacologically allowable extent.

A dose of the therapeutic agent administered to a patient is determined taking into consideration factors such as symptom severity of the patient, age, the form of the preparation, binding titer of the antibody, and the like.

When the N-terminus antibody of the present invention is used as a therapeutic agent for Alzheimer's disease, a chimeric antibody or a humanized antibody prepared from the N-terminus antibody by a conventional method is preferably used. EP0125023, EP0239400, EPO45126, WO94/20632, PUBMED ID 15316127 (Protein Eng Des Sel. 2004 May; 17(5):481-489. Epub 2004 Aug. 17), 9653494 (Ann Oncol. 1998 May; 9(5):527-34.), 1350088 (Proc Natl Acad Sci USA. 1992 May 15; 89(10):4285-9.), and the like can be referred to for preparation of the chimeric antibody and humanized antibody.

The therapeutic agent for Alzheimer's disease of the present invention obtained in this manner does not react with APP in normal cells, the agent is a safe medicine with only a low possibility of causing side reactions such as inflammation.

EXAMPLES

The present invention will be described in more detail by examples, which should not be construed as limiting the present invention. Any person having an ordinary skill in the art can easily modify or alter the inventions based on the description in this specification. Such modifications and alterations are included in the technological scope of the present invention.

Example 1

Procurement of N-Terminus Peptide and C-Terminus Peptide of Amyloid β

N-terminus peptide and C-terminus peptide of amyloid βpurified by HPLC were purchased from Synpep Corporation and TANA Laboratories, USA. The amino acid sequences of these peptides are shown in (e), (f), (g), and (h) below. The peptide (e) has cysteine (C) attached to amino acid sequence 1-16 (Sequence ID No. 1) of amyloid β, the peptide (f) has C attached to amino acid sequence 1-5 (Sequence ID No. 2) of amyloid β, the peptide (g) has KC attached to amino acid sequence 35-40 (Sequence ID No. 3) of amyloid β (1-40), and the peptide (h) has lysine-cysteine (KC) attached to amino acid sequence 38-42 (Sequence ID No. 4) of amyloid β (1-42).

| (e) | DAEFRHDSGYEVHHQKC | (Sequence ID No. 1) |
| (f) | DAEFRC | (Sequence ID No. 2) |
| (g) | KCMVGGVV | (Sequence ID No. 3) |
| (h) | KCGVVIA | (Sequence ID No. 4) |

Example 2

Preparation of Antigen for Immunization

Bound substances of each of the above peptides and thyroglobulin were prepared by the EMCS (N-(6-Maleimidocaproyloxy)-succinimide) method as follows. The molar ratio of the thyroglobulin, peptide, and EMCS used for preparing the bound substances was 1:300:400.

First, 4 mg of each peptide of Example 1 was dissolved in about 1 ml of distilled water. A solution of 5 mg of thyroglobulin in 1 ml of a 0.01 M phosphoric acid buffer (pH 7.0) and a solution of 80 μg/μl EMCS dissolved in dimethylformamide were mixed in an amount to obtain a thyroglobulin-EMCS complex solution containing the thyroglobulin and EMCS at the above molar ratio. This complex solution was divided into four portions, to each of which was added each peptide solution in an amount to make the above molar ratio, thereby obtaining a solution of a bound substance of the peptide crosslinked by EMCS and the thyroglobulin.

This bound substance solution was dialyzed using PBS to obtain a solution with a bound substance concentration of 10 µg/µl. The bound substances of each peptide and thyroglobulin obtained in this manner were used as antigens for immunization in the following examples.

Example 3

Preparation of Antibody Recognizing C-Terminus Peptide of Amyloid β (1-40)

A mouse was immunized using the bound substance of the peptide (g) and thyroglobulin obtained in Example 2 as an antigen for immunization by administering 50 µl (50 µg) of the bound substance solution at an interval of one or two weeks. The antigen was mixed with a complete Freund's adjuvant only in initial immunization and mixed with an incomplete Freund's adjuvant in the subsequent immunization. Spleen monocyte cells of the immunized mouse and a fusion partner, X63-Ag8-653, were subjected to polyethylene glycol-mediated cell fusion and hybridomas were selected using the method described in J. Immunol. 146: 3721-3728. In selecting the hybridomas, cells that react with immobilized peptide (g), but appear not reactive with peptide (h) were selected.

The cells selected in this manner were cultured in a serum-free GIT culture medium (manufactured by Wako Pure Chemical Industries, Ltd.) to produce antibodies until 80% of the cells were extinct. Next, after removing the cells from the culture medium by centrifugation (1,000 rpm, 15 min), the resultant fluid was brought to a 50% saturated state with ammonium sulfate, allowed to stand still at 4° C. overnight, and the resultant precipitate was collected by centrifugation (1,000 rpm, 30 min). After dissolving the precipitate in a twice-diluted binding buffer (manufactured by Protein AMAPS IIkit), IgG was adsorbed in Protein A column (manufactured by Pharmacia Amersham). The product was purified by PBS dialysis overnight to obtain an antibody recognizing the C-terminus peptide of amyloid β (1-40). This antibody was named 1A10.

Example 4

Confirmation of Specificity of 1A10 Antibody by Western Blotting

In order to confirm that the 1A10 antibody obtained in Example 3 recognizes the C-terminus peptide of the amyloid β (1-40), the 1A10 antibody was subjected to western blotting against each peptide of amyloid β (1-40), amyloid β (1-42), and amyloid β (1-43) according to a common western blotting method (for example, "Molecular Biology Basic Experimentation" Nankodo Co., Ltd.).

Figure 1:
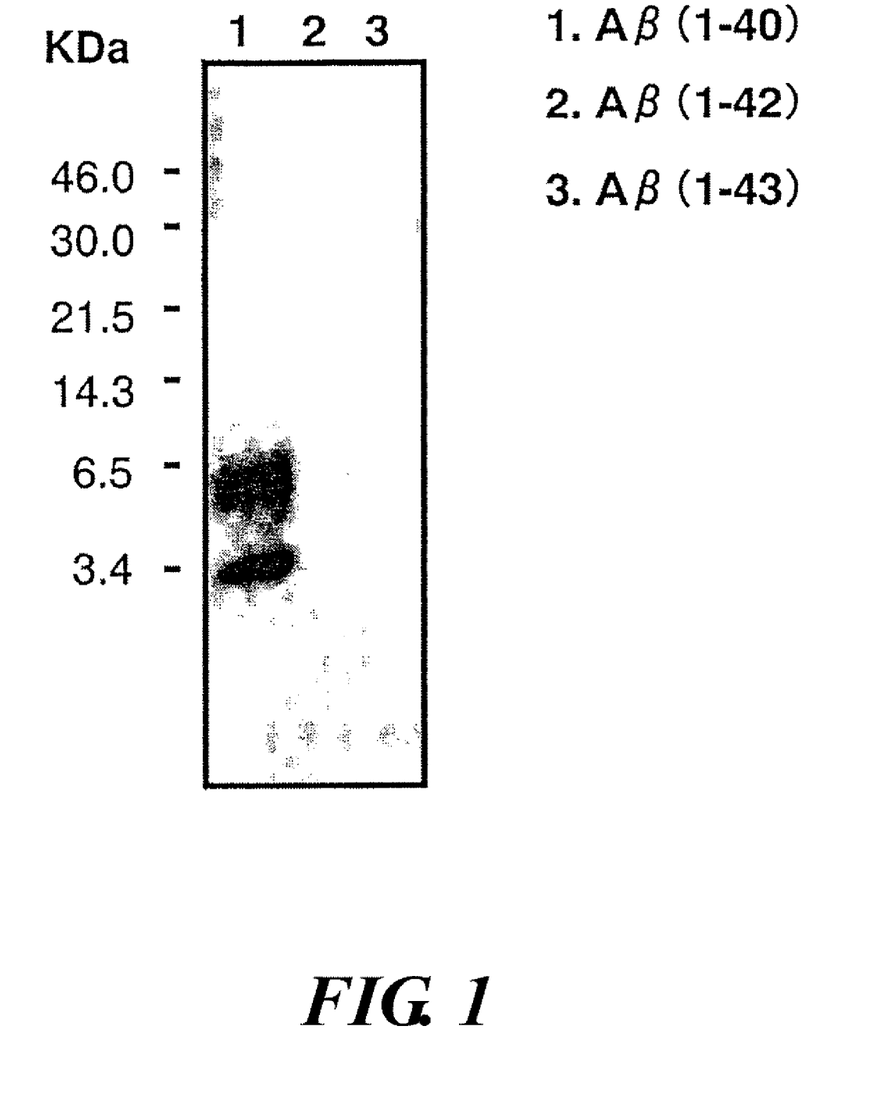
FIG. 1 is a drawing showing the specificity of the 1A10 antibody by western blotting.

The results of western blotting are shown in FIG. 1. It was confirmed that the monoclonal antibody 1A10 does not react with amyloid β (1-42) and amyloid (1-43), but recognizes only amyloid β (1-40).

Example 5

Preparation of Antibody Recognizing C-Terminus Peptide of Amyloid β (1-42)

A mouse was immunized in the same manner as in Example 3 by using the bound substance of the peptide (h) and thyroglobulin obtained in Example 2 as an antigen for immunization. Spleen monocyte cells of the immunized mouse and a fusion partner, X63-Ag8-653, were subjected to polyethylene glycol-mediated cell fusion and hybridomas were selected using the method described in J. Immunol. 146: 3721-3728. In selecting the hybridomas, cells that react with immobilized peptide (h), but appear not reactive with peptide (g) were selected.

The cells selected by the above procedure were purified in the same manner as in Example 3 to obtain an antibody recognizing the C-terminus peptide of amyloid β (1-42). This antibody was named 1C3.

A hybridoma producing antibody 1C3 and designated "Amyloid 13 Hybridoma 1C3" was deposited under the terms of the Budapest Treaty with the International Patent Organism Depositary, National Institute of Advanced Industrial Science and Technology, AIST Tsukuba Central 6, 1-1, Higashi 1-chome Tsukuba-shi, Ibaraki-ken 305-8566, Japan, on Feb. 3, 2010 and assigned accession no. FERM BP-11227.

Example 6

Confirmation of Reactivity of 1C3 Antibody by Immune-Precipitation Method

In order to confirm that the 1C3 antibody obtained in Example 5 recognizes the C-terminus peptide of the amyloid β (1-42), the 1C3 antibody was subjected to immune-precipitation against each peptide of amyloid β (1-40), amyloid β (1-41), amyloid β (1-42), and amyloid β (1-43) according to a common method (for example, "Molecular Biology Basic Experimentation" Nankodo Co., Ltd.). 6E10 antibody (manufactured by Signet Laboratories, Inc) was used for detection with a final blotting.

Figure 2:
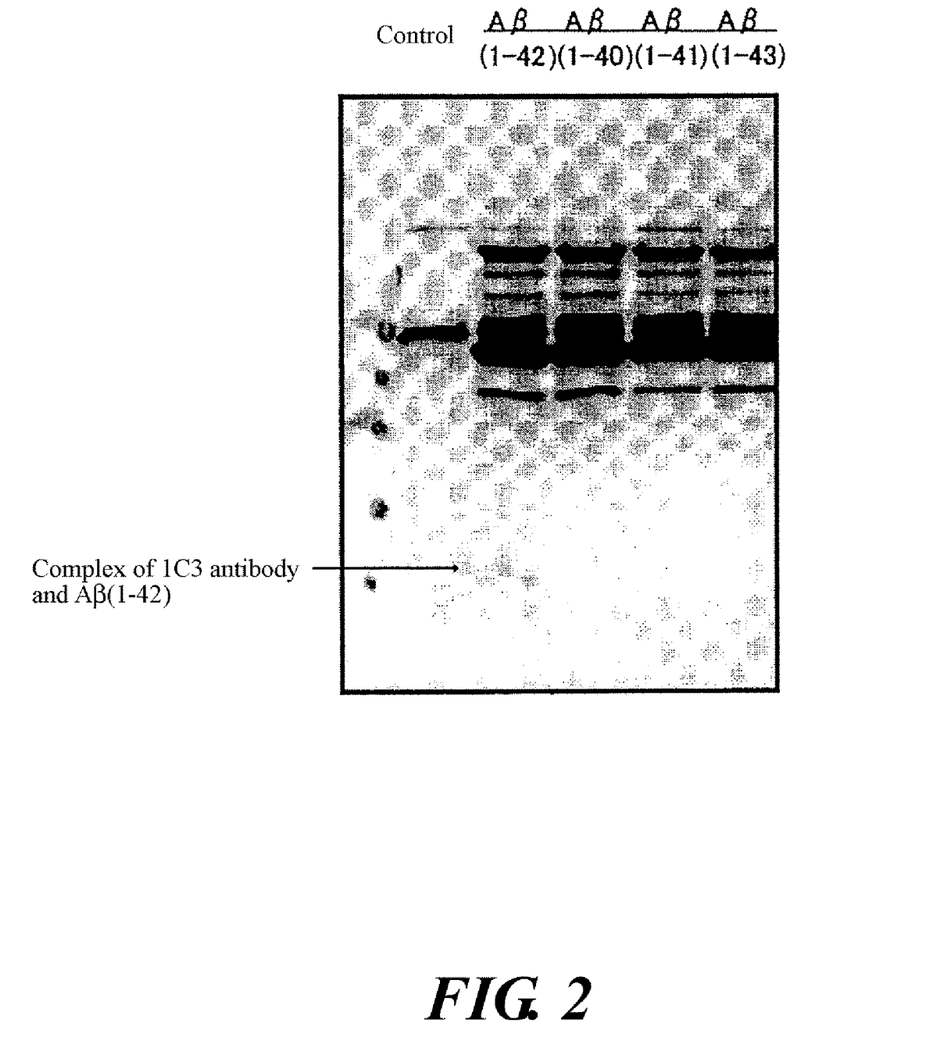
FIG. 2 is a drawing showing the specificity of the 1C3 antibody by immunological precipitation.

The results of the immune precipitation were shown in FIG. 2. It was confirmed that the antibody 1C3 specifically recognizes amyloid β (1-42), but does not recognize amyloid β (1-40), amyloid β (1-41), and amyloid β (1-43).

Example 7

Preparation of Antibody Recognizing N-Terminus Peptide of Amyloid

A BALB/c mouse was immunized by using the bound substance of the peptide (e) and thyroglobulin obtained in Example 2 as an antigen for immunization. After immunization four times, the mouse was further immunized twice using the bound substance of the peptide (f) and thyroglobulin. Spleen monocyte cells of the immunized mouse and a fusion partner, X63-Ag8-653, were subjected to polyethylene glycol-mediated cell fusion and hybridomas were selected using the method described in J. Immunol. 146: 3721-3728. In selecting the hybridomas, cells that react with immobilized peptide (e) and peptide (f) were selected.

The cells selected by the above procedure were purified in the same manner as in Example 3 to obtain an antibody recognizing the N-terminus peptide of amyloid β. This antibody was named 82E1.

Example 8

Confirmation of Specificity of 82E1 Antibody by Western Blotting

In order to confirm that the 82E1 antibody obtained in Example 7 recognizes the N-terminus peptide of the amyloid β, the 82E1 antibody was subjected to western blotting against each peptide of amyloid β (1-40), amyloid β (2-40), and amyloid β (3-40) according to a common western blotting method (for example, "Molecular Biology Basic Experimentation" Nankodo Co., Ltd.). For comparison, Chinese hamster cells in which amyloid β precursor proteins (APP) were forcibly exhibited were homogenized with a buffer solution containing 1% Triton and centrifuged to obtain a supernatant liquid, which was subjected to western blotting in the same manner as above. This supernatant contained, in addition to APP, amyloid β and βC terminal fragments (βCTF) cut from APP at the β site. In addition, for comparison with a conventional antibody, 6E10 antibody (manufactured by Signet Laboratories, Inc.) which is reported to recognize the N-terminus peptide of amyloid β was subjected to western blotting using the same sample as above.

Figure 3:
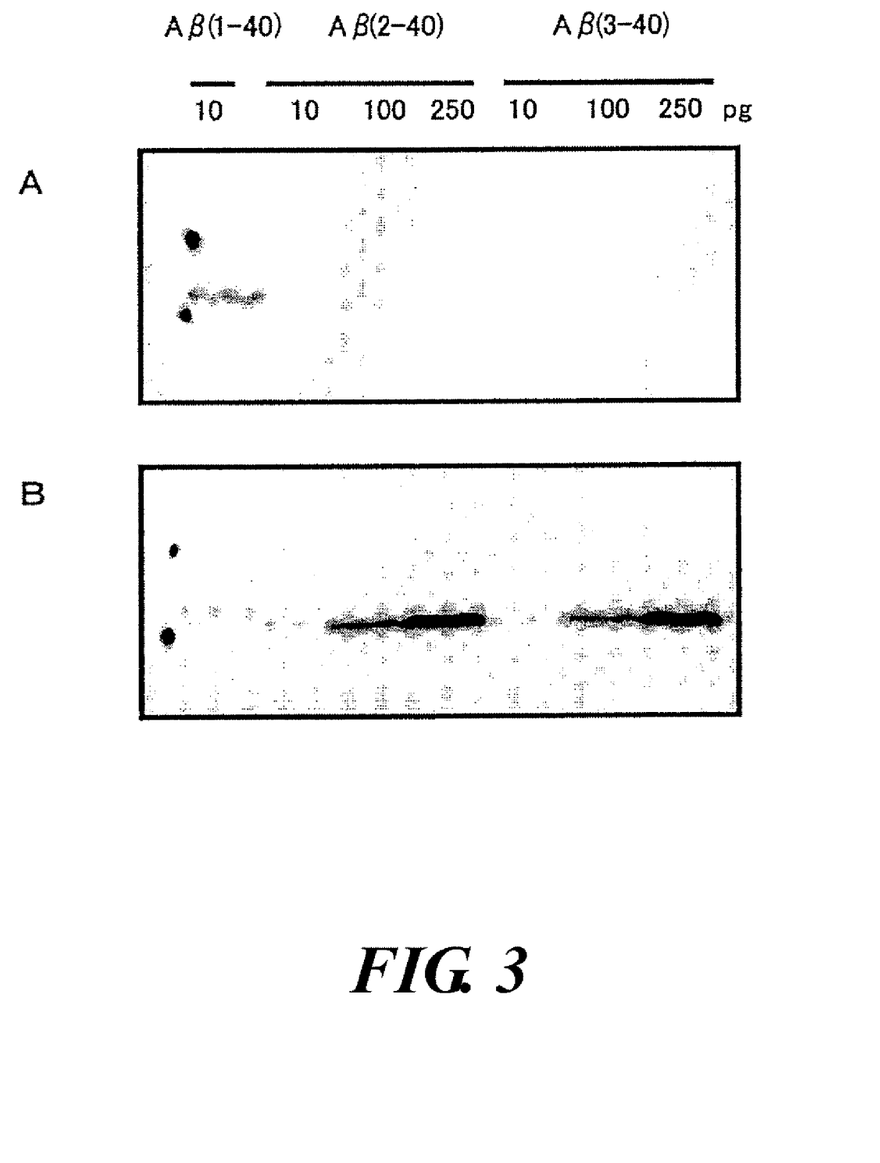
FIG. 3 is a drawing showing the specificity of the 82E1 antibody by western blotting (A: 82E1 antibody, B; 6E10 antibody).
Figure 4:
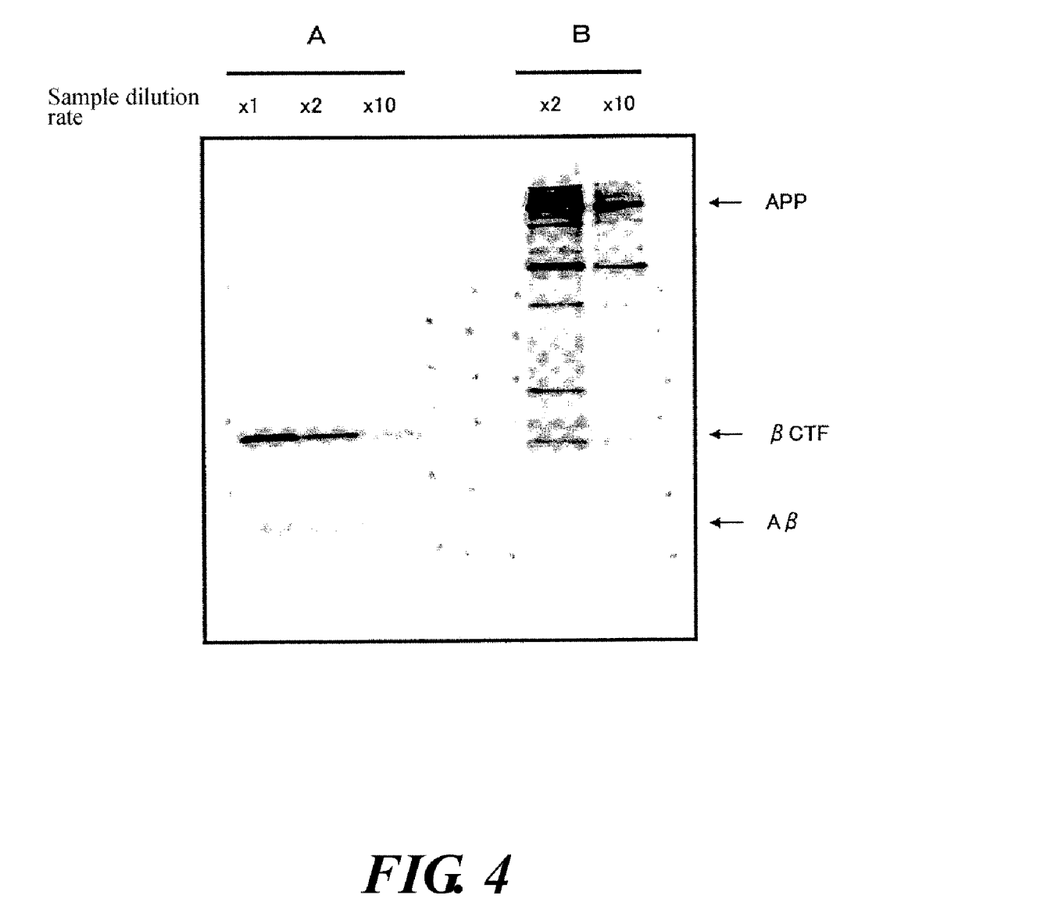
FIG. 4 is a drawing showing the specificity of the 82E1 antibody by western blotting (A: 82E1 antibody, B; 6E10 antibody).

The results of western blotting are shown in FIGS. 3 and 4. It was confirmed from FIG. 3 that the antibody 82E1 does not react with amyloid β (2-40) and amyloid β (3-40), but recognizes only amyloid β (1-40). On the other hand, 6E10 antibody was confirmed to be unreactive with amyloid β (1-40), but to recognize amyloid β (2-40) and amyloid β (3-40). In addition, based on FIG. 4, it was confirmed that 82E1 monoclonal antibody does not react with APP, but recognizes only amyloid β and βCTF. On the other hand, 6E10 antibody was confirmed to recognize APP.

Example 9

Preparation of Bound Substance of Antibody Recognizing N-Terminus Peptide of Amyloid β (82E1 Antibody) and HRP The bound substance of the 82E1 antibody obtained in Example 7 and HRP was prepared as follows. A necessary amount of HRP was dissolved in distilled water, oxidized with NaIO4, and dialyzed with a 1 mM acetic acid buffer solution (pH 4.4) overnight. 2 mg of 82E1 antibody was also dialyzed with a 0.1 M carboxylic acid buffer solution (pH 9.5) overnight. The dialyzed 82E1 antibody and HRP were mixed at a ratio of 0.4 mg of HRP to 1 mg of the antibody and reacted at room temperature for two hours. NaBH4 was added to the reaction mixture. After reaction in ice for two hours, the resulting reaction product was dialyzed with PBS overnight. The reaction product was further subjected to gel permeation to obtain a bound substance of the 82E1 antibody and HRP.

Example 10

Construction of Sandwich ELISA Method

The sandwich ELISA method using the antibodies obtained in the above Examples was constructed as follows. 20 μg/ml A10 antibody or 1C3 antibody was added to 96-well plates for ELISA analysis in an amount of 100 μl each. The antibodies were incubated at 4° C. overnight, followed by blocking using a 1% BSA/PBS/NaN3 solution, to obtain a plate for the sandwich ELISA method. The bound substance of the 82E1 antibody obtained in Example 7 and HRP was used as the labeled antibody.

Figure 5:
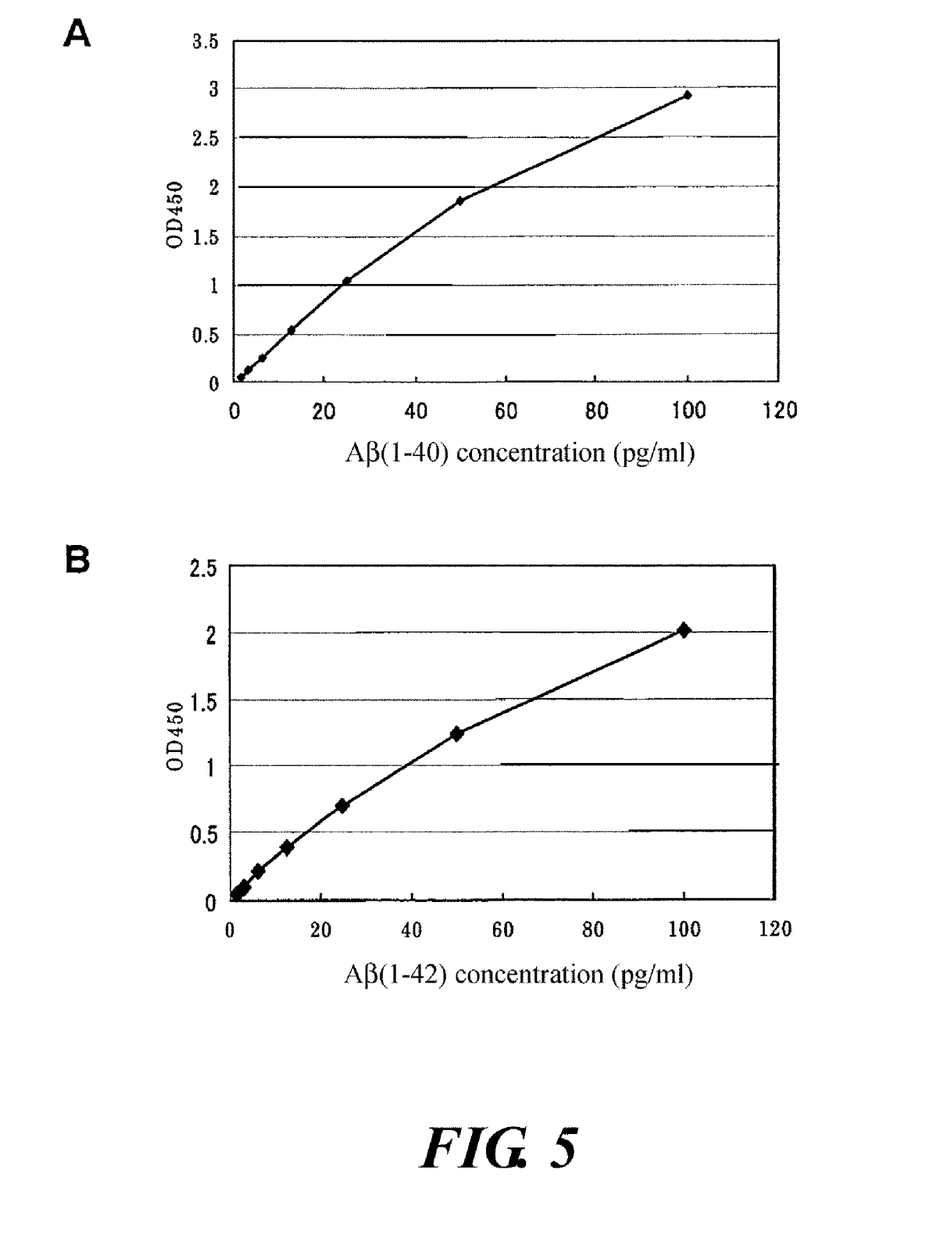
FIG. 5 shows the results of standard curves obtained by assaying a synthetic amyloid β using an ELISA kit prepared in Example 10, wherein A shows the result of assaying a synthetic amyloid β (1-40) using a combination of the 1A10 antibody and HRP labeled 82E1 antibody and B is a result of assaying a synthetic amyloid β (1-42) using a combination of the 1C3 antibody and HRP labeled 82E1 antibody.

The peptides of the synthetic amyloid β (1-40) and synthetic amyloid β (1-42) were respectively assayed using the ELISA plate and labeled antibody. The resulting standard curves are shown in FIG. 5. In FIG. 5, A is a result of assaying the synthetic amyloid β (1-40) using the combination of the 1A10 antibody and HRP labeled 82E1 antibody and B is a result of assaying the synthetic amyloid β (1-42) using the combination of the 1C3 antibody and HRP labeled 82E1 antibody. Both results exhibited an excellent concentration-depending linearity.

Example 11

Amyloid β Precipitation Inhibition Test

82E1 antibody obtained in Example 7 was diluted with PBS to a concentration of 1 mg/ml and abdominally injected to 16-month old Tg2576 genetically engineered mice (n=3) exhibiting amyloid βrecursor proteins (APP), at a dose of 10 mg/Kg (mouth body weight) once every week. As a control, only PBS was dosed to mice (n=2) in the same manner. The mice to which the 82E1 antibody or PBS was administered twelve times (for about three months) were sacrificed. The left cerebral hemisphere was fixed with a 4% formaldehyde buffer solution and paraffin was embedded. 5 μm continuous segments were prepared from the paraffin-embedded cerebral tissue and immunologically stained with amyloid β (1-40) polyclonal antibody and amyloid β (1-42) polyclonal antibody (both manufactured by Immuno-Biological Laboratories Co., Ltd., product numbers 18580 and 18582). The results are shown in FIGS. 6 and 7.

Figure 8:
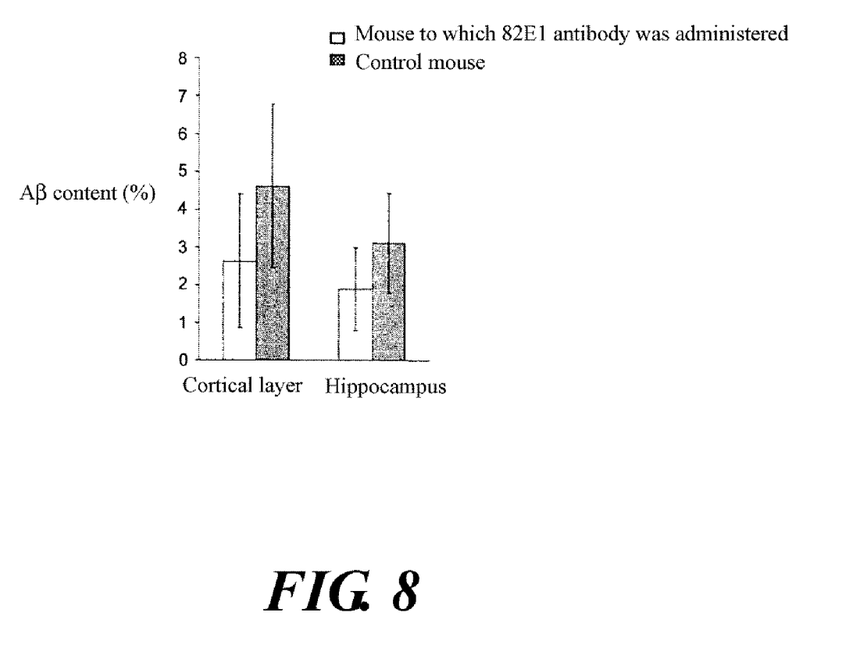
FIG. 8 is a drawing showing deposition of amyloid β (1-40) and amyloid β (1-42) in segments, in terms of the proportion (%) of the immunological staining positive region in the entire region.

Ten segments from the cortical layer and five segments from the hippocampus were selected and submitted to imaging analysis using a microscopic digital camera and simple PCI software (Compix, Inc. Imaging Systems, USA). Deposition of amyloid β (1-40) and amyloid β (1-42) was indicated by the proportion (%) of the immunological staining positive region in the entire region. The results are shown in FIG. 8.

Figure 9:
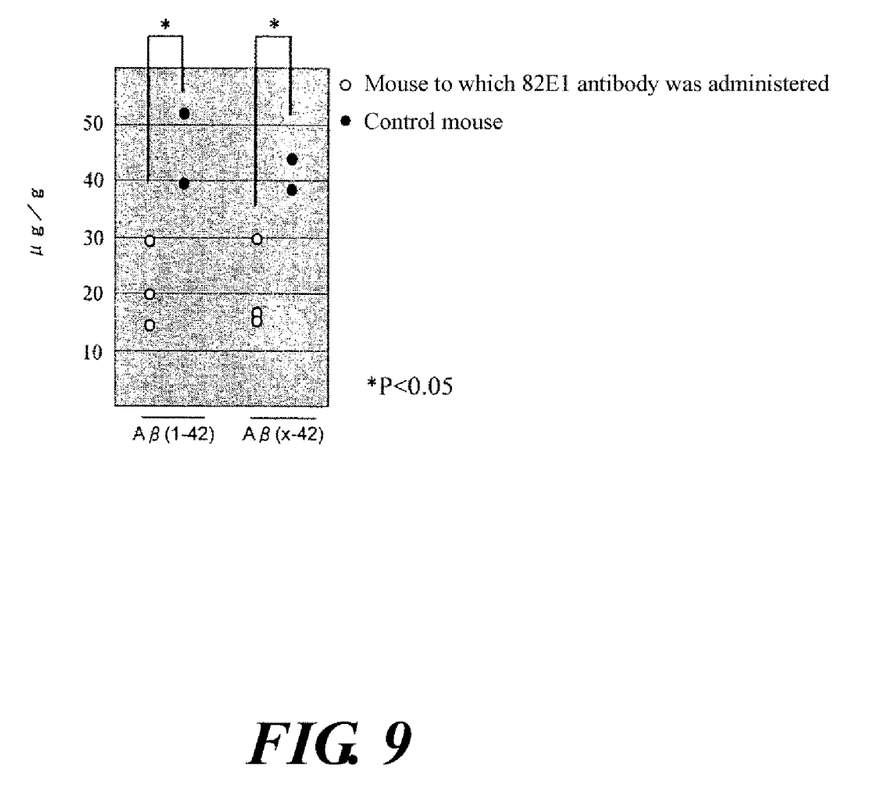
FIG. 9 is a drawing showing the results of ELISA assay of amyloid β (1-42) and amyloid β (x-42) in the brain.

In addition, amyloid β insoluble in a 0.05 M Tris HCl buffered physiological saline solution (TBS, pH 7.6) was extracted from the frontal right of the head (¼ of the brain) with 6 M guanidine-hydrochloric acid to measure amyloid β (x-42) using an assay kit of amyloid β (1-42) and human amyloid β (1-42) (manufactured by Immuno-Biological Laboratories Co., Ltd., Product No. 17711) in the sandwich ELISA system prepared in Example 10. The method described by M. Morishima, Kawashima, et al., in Am. J. Pathol., 157 (2000) 2093-2099 was followed for extraction. The results are shown in FIG. 9.

Figure 6:
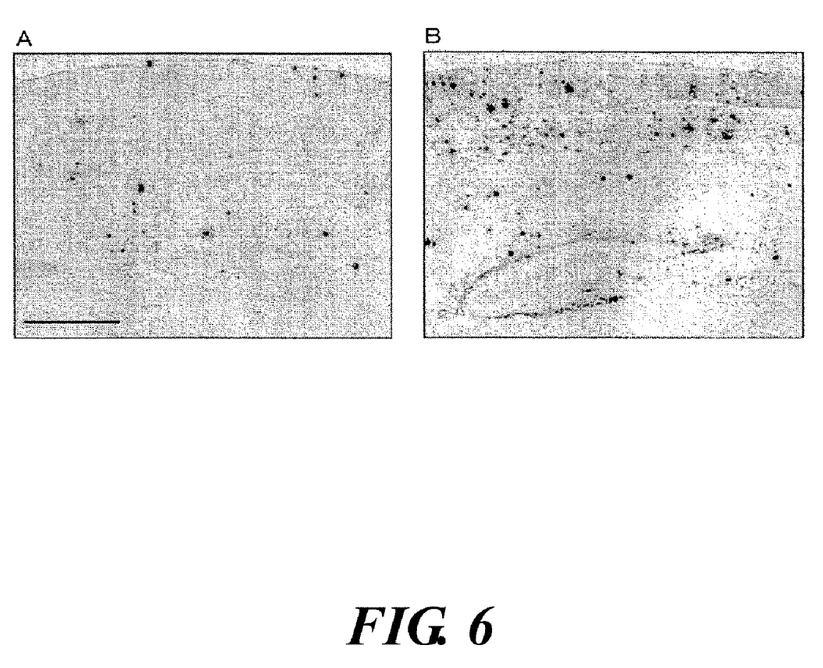
FIG. 6 is a drawing showing the results of immunological staining of the left cerebral hemisphere, including the cortical layer and hippocampus (A: mouse to which the 82E1 antibody was administered, B: control mouse).
Figure 7:
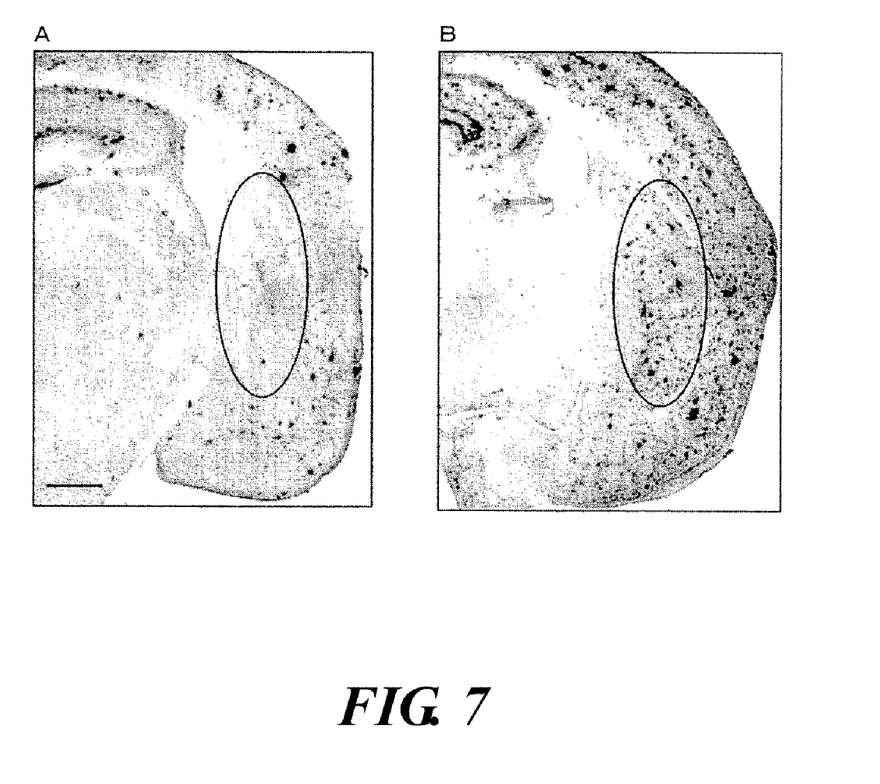
FIG. 7 is a drawing showing the results of immunological staining of the left cerebral hemisphere (basal nuclei) (A: mouse to which the 82E1 antibody was administered, B: control mouse).

It can be seen from the images of immunologically stained amyloid β (1-42) that the number of senile plaques was smaller in the brain of the mouse to which the 82E1 was administered as compared with that in the control (FIG. 6). In the basal nuclei in which the amyloid β deposits slower than in the cortical layer or hippocampus, the number of senile plaques was clearly smaller in the mouse to which the 82E1 was administered as compared with that in the control (FIG. 7). This was also confirmed by the image analyzer (FIG. 8). The amount of amyloid β deposited in the mouse to which the 82E1 was administered was significantly decreased in both the amyloid β (1-40) (a decrease of 30% in the cortical layer and 40% in the hippocampus (for both $p<0.05$)) and the amyloid β (1-42) (a decrease of 43% in the cortical layer ($p<0.01$) and 40% in the hippocampus ($p<0.05$)). In addition, as a result of assaying amyloid β (1-42) and amyloid β (x-42) in the brain by the ELISA method (FIG. 9), the amounts significantly decreased in the mouse to which the 82E1 was administered (both decreased 50% (for both $p<0.05$)).

INDUSTRIAL APPLICABILITY

The antibody which recognizes the N-terminus peptide of an amyloid of the present invention recognizes the amyloid β, but does not recognize an amyloid precursor protein.

Therefore, the amyloid β assay kit using this antibody can precisely assay the amyloid β (1-40) or amyloid β (1-42) possessing a complete length unlike amyloid assay kits heretofore made commercially available.

In addition, the amyloid β assay kit can be used for diagnosing Alzheimer's disease in which the amyloid β is involved and studies on the mechanism and the like of Alzheimer's disease occurrence. One specific example that can be given is search of β secretase inhibitors.

Furthermore, because the therapeutic agent for Alzheimer's disease using the antibody does not react with amyloid β precursor proteins in normal cells notwithstanding its capability of inhibiting deposition of amyloid β, the agent is an excellent medicine with only a low possibility of causing side reactions such as inflammation.

The invention claimed is:

1. A monoclonal antibody that recognizes an amyloid β—that is the monoclonal antibody designated 1C3, or a chimeric or humanized form of the antibody designated 1C3.

2. The monoclonal antibody of claim 1 that is the humanized form of the monoclonal antibody designated 1C3.

3. The monoclonal antibody of claim 1 that is the monoclonal antibody designated 1C3.

4. A pharmaceutical composition comprising the monoclonal antibody of claim 1 and one or more pharmaceutically acceptable carriers or additives.

5. A method of treating a disease induced by accumulation of amyloid β comprising administering the monoclonal antibody of claim 1 to an individual in need of such treatment.

6. The method of claim 5 wherein said disease is Alzheimer's disease.

7. A method of inhibiting deposition of amyloid β comprising administering the monoclonal antibody of claim 1 to an individual in need of such inhibition.

8. A method of treating a disease induced by accumulation of amyloid β comprising administering the monoclonal antibody of claim 2 to an individual in need of such treatment.

9. The method of claim 5 wherein said disease is Alzheimer's disease.

10. A method of inhibiting deposition of amyloid β comprising administering the monoclonal antibody of claim 2 to an individual in need of such inhibition.

* * * * *

SEQUENCE LISTING

```
<160> NUMBER OF SEQ ID NOS: 6

<210> SEQ ID NO 1
<211> LENGTH: 16
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

<210> SEQ ID NO 2
<211> LENGTH: 5
<212> TYPE: PRT
<213> ORGANISM: Homo sapiens

<400> SEQUENCE: 2

Asp Ala Glu Phe Arg
1               5

<210> SEQ ID NO 3
<211> LENGTH: 6
<212> TYPE: PRT
<213> ORGANISM: Homo sapiens

<400> SEQUENCE: 3

Met Val Gly Gly Val Val
1               5

<210> SEQ ID NO 4
<211> LENGTH: 5
<212> TYPE: PRT
<213> ORGANISM: Homo sapiens

<400> SEQUENCE: 4

Gly Val Val Ile Ala
1               5
```

```
-continued

<210> SEQ ID NO 5
<211> LENGTH: 40
<212> TYPE: PRT
<213> ORGANISM: Homo sapiens

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 6
<211> LENGTH: 42
<212> TYPE: PRT
<213> ORGANISM: Homo sapiens

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```